United States Patent
Yan et al.

(10) Patent No.: US 11,938,345 B2
(45) Date of Patent: Mar. 26, 2024

(54) METHOD AND APPARATUS FOR ADJUSTING POSITION, STORAGE MEDIUM, AND RADIOTHERAPY SYSTEM

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Hao Yan, Xi'an (CN); Tianchang Gou, Xi'an (CN); Jiuliang Li, Xi'an (CN); Jinsheng Li, Shenzhen (CN)

(73) Assignees: OUR UNITED CORPORATION, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 519 days.

(21) Appl. No.: 17/266,545

(22) PCT Filed: Aug. 7, 2018

(86) PCT No.: PCT/CN2018/099245
§ 371 (c)(1),
(2) Date: Feb. 5, 2021

(87) PCT Pub. No.: WO2020/029089
PCT Pub. Date: Feb. 13, 2020

(65) Prior Publication Data
US 2021/0316159 A1   Oct. 14, 2021

(51) Int. Cl.
*A61N 5/10* (2006.01)

(52) U.S. Cl.
CPC .... *A61N 5/1049* (2013.01); *A61N 2005/1051* (2013.01)

(58) Field of Classification Search
None
See application file for complete search history.

(56) References Cited

U.S. PATENT DOCUMENTS

| 2005/0101860 A1* | 5/2005 | Patrick | A61N 5/1015 |
| | | | 600/433 |
| 2010/0158198 A1* | 6/2010 | Jeung | A61B 6/032 |
| | | | 378/204 |

(Continued)

FOREIGN PATENT DOCUMENTS

| CN | 103284743 A | 9/2013 |
| CN | 104338238 A | 2/2015 |

(Continued)

OTHER PUBLICATIONS

International search report of PCT application No. PCT/CN2018/099245 dated Mar. 21, 2019.

(Continued)

*Primary Examiner* — Edwin C Gunberg
(74) *Attorney, Agent, or Firm* — Knobbe, Martens, Olson & Bear LLP

(57) ABSTRACT

A method for adjusting a position, including: acquiring a real-time position of a positioning marker preset at an affected part; acquiring a reference position of the positioning marker; and outputting position adjustment information, by means of a display and/or a voice, based on the real-time position and the reference position. The position adjustment information is configured to prompt a patient to adjust his/her position.

16 Claims, 6 Drawing Sheets

(56) References Cited

U.S. PATENT DOCUMENTS

2014/0275698 A1 9/2014 Lidström et al.
2017/0196482 A1 7/2017 Matsumoto et al.

FOREIGN PATENT DOCUMENTS

| CN | 105324155 A | 2/2016 |
| CN | 105342631 A | 2/2016 |
| CN | 108273199 A | 7/2018 |
| WO | 2015186586 A1 | 12/2015 |

OTHER PUBLICATIONS

Second office action of Chinese application No. 201880095821.4 dated Mar. 21, 2022.

* cited by examiner

METHOD AND APPARATUS FOR ADJUSTING POSITION, STORAGE MEDIUM, AND RADIOTHERAPY SYSTEM

CROSS-REFERENCE TO RELATED APPLICATION

This application is a US national phase application of PCT Application No. PCT/CN2018/099245, filed on Aug. 7, 2018, the entire contents of which are incorporated herein by reference.

TECHNICAL FIELD

The present disclosure relates to the field of radiation therapy, and in particular, to a method and apparatus for adjusting a position and a radiation therapy system.

BACKGROUND

A radiation therapy is a method for treating tumour through a radiation therapy device. However, since a patient may move in a process of the radiation therapy, or a positioning is not accurate enough in the process of positioning the patient, the precision of radiation therapy is affected.

SUMMARY

In a first aspect, a method for adjusting a position is provided. The method includes:
acquiring a real-time position of a positioning marker preset at an affected part;
acquiring a reference position of the positioning marker; and
outputting position adjustment information, by means of a display and/or a voice, based on the real-time position and the reference position, wherein the position adjustment information is configured to prompt a patient to adjust his/her position.

In a second aspect, an apparatus for adjusting a position is provided. The apparatus includes a processor and a memory, wherein the memory stores an instruction therein which is loaded and executed by the processor to implement the method for adjusting the position as descried in the first aspect.

In a third aspect, a storage medium is provided. The storage medium stores an instruction therein. The readable storage medium, when running on a processing component, enables the processing component to perform the method for adjusting the position as descried in the first aspect.

In a fourth aspect, a radiation therapy system is provided. The radiation therapy system includes the apparatus for adjusting the position as descried in the second aspect and a position tracking system.

BRIEF DESCRIPTION OF THE DRAWINGS

The accompanying drawings here, which are incorporated in and constitute a part of this description, illustrate embodiments consistent with the present disclosure and, together with the description, serve to explain the principles of the present disclosure.

DETAILED DESCRIPTION

For clearer descriptions of the objectives, technical solutions and advantages in the present disclosure, the embodiments of the present disclosure are described in further detail below with reference to the accompanying drawings.

At present, for ensuring the precision of the radiation therapy, a positioning marker is usually disposed on a body surface of the patient. When it is detected that the positioning marker deviates from a reference position, a control system prompts the radiation therapy device to adjust a position of a treatment couch, so that the positioning marker coincides with the reference position all the time.

However, if the patient moves frequently, the position of the treatment couch needs to be adjusted constantly, but the constant movement of the treatment couch may cause accumulated mechanical errors, resulting in low precision when the treatment couch is moved. Hence, the precision of radiation therapy is affected.

Figure 1:
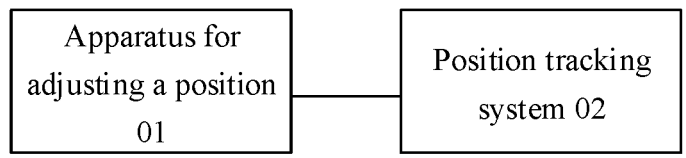
FIG. 1 is a structural diagram of a radiation therapy system according to an embodiment of the present disclosure.

FIG. 1 is a structural diagram of a radiation therapy system according to an embodiment of the present disclosure. As shown in FIG. 1, the radiation therapy system may include: an apparatus 01 for adjusting a position (which may also be called an interactive motion management apparatus) and a position tracking system 02 (such as an optical infrared tracking system).

The position tracking system 02 is configured to track a position of a positioning marker (such as a small infrared sphere) preset at an affected part (such as the head or body) in real time. The apparatus 01 for adjusting the position is configured to acquire a real-time position of the positioning marker preset at the affected part, and output position adjustment information for prompting a patient to adjust his/her position, by means of a display and/or a voice, based on the real-time position and a reference position.

In one embodiment, referring to FIG. 1, the apparatus 01 for adjusting the position is connected to the position tracking system 02, and may directly acquire in real time the real-time position of the positioning marker preset at the affected part from the position tracking system 02. In another embodiment, the position tracking system 02 and the apparatus 01 for adjusting the position are connected to a control system. In this way, the position tracking system 02 sends in real time the real-time position of the positioning marker preset at the affected part to the control system, and the apparatus 01 for adjusting the position acquires in real time the real-time position of the positioning marker preset at the affected part from the control system. Certainly, the position tracking system 02 may also be integrated in the control system and the real-time position of the positioning marker preset at the affected part is acquired from the position tracking system 02; or the position tracking system 02 is integrated in the apparatus 01 for adjusting the position, and the apparatus 01 for adjusting the position directly acquires the real-time position of the positioning marker preset at the affected part. Thus, the production cost of the radiation therapy system is reduced.

Figure 2:
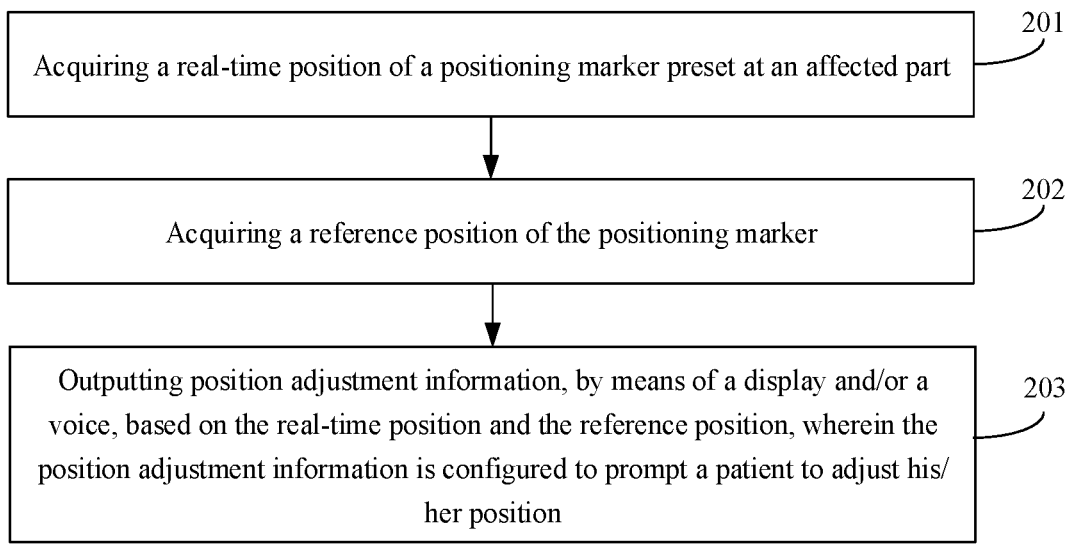
FIG. 2 is a flowchart of a method for adjusting a position according to an embodiment of the present disclosure.

FIG. 2 is a flowchart of a method for adjusting a position according to an embodiment of the present disclosure. The method is applicable to the apparatus 01 for adjusting the position shown in FIG. 1. The description is given with an example that the method for adjusting the position is applicable to a radiation therapy process. As shown in FIG. 2, the method may include the following steps.

In step 201, a real-time position of a positioning marker preset at an affected part is acquired.

As the patient may have an unexpected small action or movement in the process of radiation therapy, a position of the positioning marker preset at the affected part deviates, and thus the precision of radiation therapy is affected. Therefore, for detecting whether there is a deviation between the position of the positioning marker and a reference position to ensure the precision of radiation therapy, the position tracking system 02 may detect the real-time position of the positioning marker in real time. The apparatus 01 for adjusting the position may acquire in real time the real-time position of the positioning marker detected by the position tracking system 02.

In step 202, a reference position of the positioning marker is acquired.

In the embodiment of the present disclosure, the reference position of the positioning marker refers to a position of the positioning marker after the patient has been positioned before radiation therapy.

Since whether the positioning marker deviates cannot be determined by only acquiring the real-time position of the positioning marker, in the embodiment of the present disclosure, the apparatus 01 for adjusting the position may also acquire the reference position of the positioning marker in advance. When the real-time position of the positioning marker does not coincide with the reference position, it may be determined that the positioning marker deviates. When the real-time position of the positioning marker coincides with the reference position, it may be determined that the positioning marker does not deviate.

In step 203, position adjustment information is output based on the real-time position and the reference position by means of a display and/or a voice, wherein the position adjustment information is configured to prompt the patient to adjust his/her position.

In the embodiment of the present disclosure, the apparatus 01 for adjusting the position may output the position adjustment information for prompting the patient to adjust his/her position, by means of the display and/or the voice, based on the acquired real-time position and reference position of the positioning marker.

Optionally, the acquired real-time position and reference position of the positioning marker at the affected part are considered as the position adjustment information and are displayed to the patient by the apparatus 01 for adjusting the position, so that the patient adjusts his/her position by himself/herself based on the observed real-time position and reference position. And/or the apparatus 01 for adjusting the position may determine a positioning adjustment mode based on the real-time position and the reference position, and output the position adjustment information including the position adjustment mode by means of the voice. The patient may adjust his/her position by himself/herself based on the received position adjustment mode.

As the apparatus 01 for adjusting the position may acquire the real-time position of the positioning marker in real time, after the patient adjusts his/her position, the apparatus 01 for adjusting the position may continue to output the position adjustment information based on the real-time position of the adjusted positioning marker, so that the patient may continue to pertinently adjust his/her position based on the position adjustment information output again by the apparatus 01 for adjusting the position, i.e., based on a real-time adjustment situation of the patient self.

In summary, in the method for adjusting the position according to the embodiment of the present disclosure, the position adjustment information for prompting the patient to adjust his/her position may be output, by means of the display and/or the voice, based on the acquired real-time position of the positioning marker preset at the affected part and the acquired reference position of the positioning marker. As the method may allow the patient to adjust his/her position by himself/herself based on the output position adjustment information, there is no need for frequently moving a treatment couch. Therefore, the problem that the precision of radiation therapy is affected due to an accumulated mechanical error caused by constantly moving the treatment couch is avoided.

Figure 3:
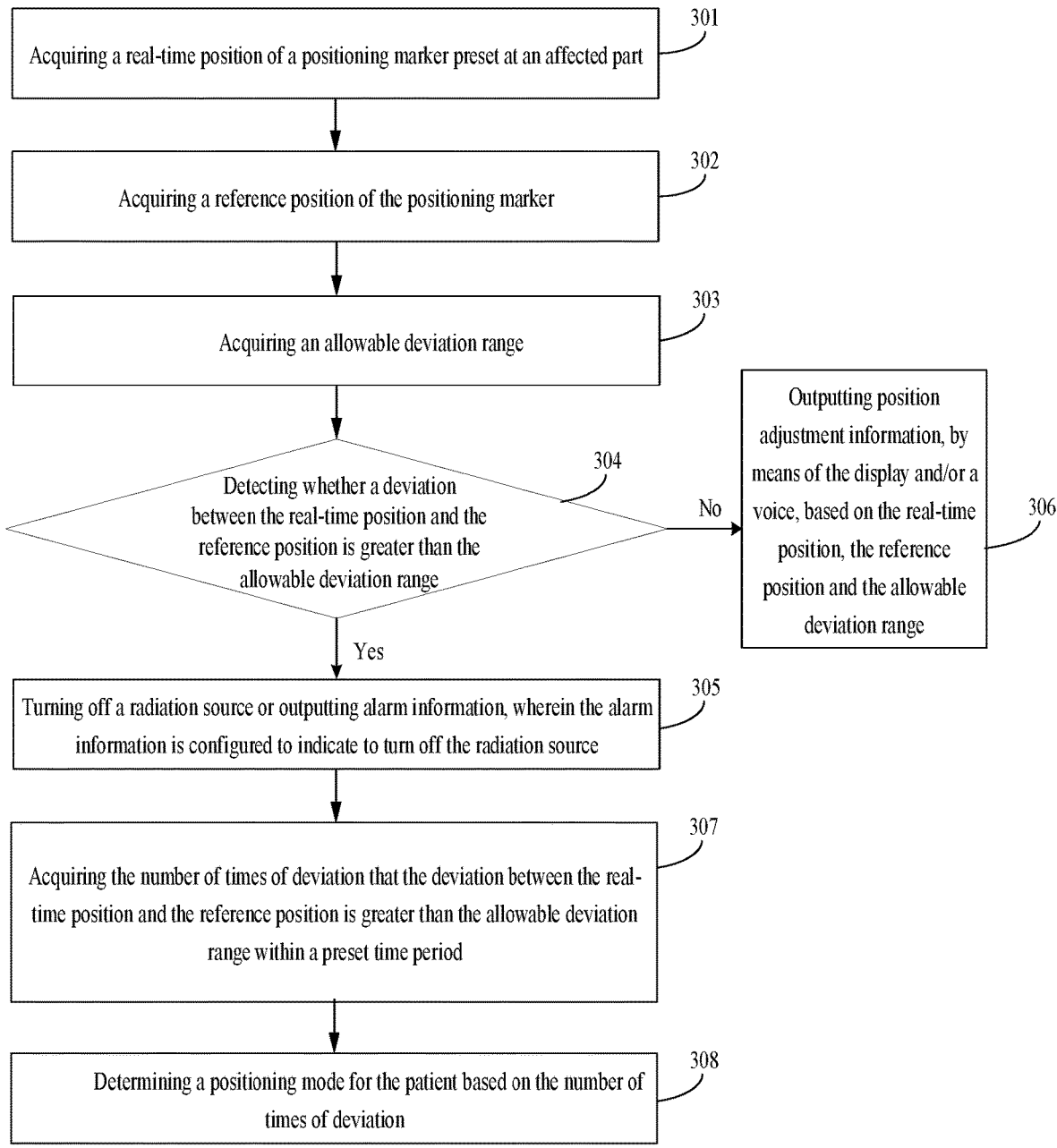
FIG. 3 is a flowchart of another method for adjusting a position according to an embodiment of the present disclosure.

FIG. 3 is a flowchart of another method for adjusting a position according to an embodiment of the present disclosure. The method is applicable to the apparatus 01 for adjusting the position shown in FIG. 1. The description is given with an example that the method for adjusting the position is applicable to a radiation therapy process. As shown in FIG. 3, the method may include the following steps.

In step 301, a real-time position of a positioning marker preset at an affected part is acquired.

As the patient may have an unexpected small action or movement in the process of radiation therapy, a position of the positioning marker preset at the affected part deviates, and thus the precision of radiation therapy is affected. Therefore, for detecting whether there is a deviation between the position of the positioning marker and a reference position, the position tracking system 02 may detect the real-time position of the positioning marker in real time. The apparatus 01 for adjusting the position may acquire in real time the real-time position of the positioning marker detected by the position tracking system 02.

In step 302, a reference position of the positioning marker is acquired.

In the embodiment of the present disclosure, the reference position of the positioning marker refers to a position of the positioning marker after the patient has been positioned before radiation therapy. In addition, the reference position of the positioning marker acquired by the apparatus 01 for adjusting the position may be coordinate values of the positioning marker in a designated coordinate system. The designated coordinate system may be a device coordinate system. A radiation therapy system generally includes a radiation therapy device and a position tracking system. Therefore, the designated coordinate system may be a device coordinate system corresponding to the radiation therapy device or an infrared coordinate system of the position tracking system.

Since whether the positioning marker deviates cannot be determined by only acquiring the real-time position of the positioning marker, in the embodiment of the present disclosure, the apparatus 01 for adjusting the position may also acquire the reference position of the positioning marker in advance. When the real-time position of the positioning marker does not coincide with the reference position, it may be determined that the positioning marker deviates. When the real-time position of the positioning marker coincides with the reference position, it may be determined that the positioning marker does not deviate.

As one optional embodiment, the apparatus 01 for adjusting the position may acquire a position of the positioning marker after the patient has been positioned, and determine the acquired position as the reference position.

In the embodiment of the present disclosure, before radiation therapy, the positioning marker may be disposed on the body surface of the patient and then the patient is positioned, so that a target point of the affected part of the patient is aligned with a radiation focus of the radiation therapy device. After the positioning is completed, the apparatus 01 for adjusting the position may directly acquire the position of the positioning marker, and determine this position as the reference position of the positioning marker, or after the patient has been positioned, the apparatus 01 for adjusting the position may also receive the position of the positioning marker acquired by the position tracking system 02, and determine this position as the reference position.

As another optional embodiment, the apparatus 01 for adjusting the position may acquire the reference position from a treatment plan before radiation therapy.

The treatment plan refers to a treatment plan made for the patient by a treating physician after the treating physician examines the patient. For example, before radiation therapy is performed on the patient, the patient may be subjected to computed tomography (CT) scanning firstly to acquire a CT image of the patient. The treating physician may acquire the situation about the affected part (such as the position and size of the affected part) of the patient from the CT image. Further, the treating physician may record the reference position of the positioning marker of the affected part in the treatment plan based on the CT image, and input the reference position of the positioning marker to the apparatus 01 for adjusting the position. A storage space of the apparatus 01 for adjusting the position may be reduced by receiving the reference position input by the treating physician based on the treatment plan.

Or the treating physician may also pre-store the made treatment plan in the apparatus 01 for adjusting the position before radiation therapy, so that the apparatus 01 for adjusting the position may directly acquire the reference position of the positioning marker from the treatment plan. The acquisition efficiency may be improved by acquiring the reference position of the positioning marker from the treatment plan. In addition, the production cost of the radiation therapy system is reduced as there is no need for specifically disposing the position tracking system 02 for acquiring the reference position.

Optionally, in the embodiment of the present disclosure, the apparatus 01 for adjusting the position may also store a corresponding relationship among identity information and affected part information of the patient and the reference position of the positioning marker. Thus, when making the treatment plan for a certain patient, the treating physician may determine the reference position of the positioning marker corresponding to this patient based on the acquired identity information and affected part information of the patient and with reference to the corresponding relationship stored in the apparatus 01 for adjusting the position. That is, the treating physician may acquire the reference position of the positioning marker corresponding to a patient, who has the similar or the same identity information and the affected part information of the patient from the corresponding relationship, and determine the acquired reference position as the reference position of the positioning marker of the patient.

In step 303, an allowable deviation range is acquired.

In the embodiment of the present disclosure, during the radiation therapy process, when a movement range of the patient is relatively smaller, that is, a deviation between the real-time position and the reference position of the positioning marker is relatively smaller, there may be no deviation between the position of the positioning marker and the reference position. At this time, the radiation therapy will not be greatly affected, and thus the patient may not need to adjust his/her position.

When the movement range of the patient is relatively larger, that is, the deviation between the real-time position and the reference position of the positioning marker is relatively larger, a deviation between the position of the positioning marker and the reference position is also relatively larger. At this time, a radiation source may need to be turned off immediately to prevent injury to normal tissues of the patient.

Therefore, in the embodiment of the present disclosure, the apparatus 01 for adjusting the position may also acquire the allowable deviation range of the positioning marker, so as to determine whether the position needs to be adjusted or determine whether the radiation therapy needs to be stopped based on the allowable deviation range. In addition, the allowable deviation range acquired by the apparatus 01 for adjusting the position may be an upper limit of a distance value from the reference position of the positioning marker in the designated coordinate system.

As one optional embodiment, the apparatus 01 for adjusting the position may pre-store a corresponding relationship among the identity information and the affected part information of the patient and the allowable deviation range. The allowable deviation range in this corresponding relationship may be set in advance by the treating physician. The apparatus 01 for adjusting the position may determine the allowable deviation range corresponding to the current patient based on the acquired identity information and affected part information of the patient. The efficiency of acquiring the allowable deviation range may be improved by directly acquiring the allowable deviation range from the pre-stored corresponding relationship. The identity information may include at least one of the patient's age and the patient's gender; and the affected part information may include at least one of a tumor type, a tumor position, and a tumor size of the affected part.

For example, it is assumed that the identity information of the patient stored in the apparatus 01 for adjusting the position includes the patient's age and the patient's gender, and the affected part information of the patient stored in the position adjustment apparatus 01 includes the tumor position. Correspondingly, the corresponding relationship among the identity information and the affected part information of the patient and the allowable deviation range stored in the apparatus 01 for adjusting the position may be as shown in table 1. For example, referring to table 1, the identity information of a certain patient is a 4-year-old male; the affected part information of the patient is a lung tumor; and the allowable deviation range corresponding to the affected part information and the identity information may be 0 to x1 mm.

TABLE 1

| Affected Part Information | Identity Information | Allowable Deviation Range |
| --- | --- | --- |
| Lung Tumor | 4-year-old male | 0 to x1 mm |
| Brain Tumor | 24-year-old female | 0 to x2 mm |

Further, it is assumed that before radiation therapy, the identify information and the affected part information of a certain patient which are acquired by the apparatus 01 for adjusting the position are a 24-year-old female and a brain tumor respectively, the apparatus 01 for adjusting the position may directly determine that the allowable deviation range corresponding to this patient is 0 to x2 mm based on the corresponding relationship shown in table 1 above.

It should be noted that in the embodiment of the present disclosure, when performing radiation therapy on the patient, the treating physician may also adjust in real time the allowable deviation range determined by the apparatus 01 for adjusting the position with reference to an actual movement range and the number of times of movement of the patient.

As another optional embodiment, the apparatus 01 for adjusting the position may receive the allowable deviation range input by the treating physician. That is, the treating physician may determine the allowable deviation range corresponding to the patient for the patient in advance based on the patient information and the affected part information. The reliability and pertinence of the acquired allowable deviation range may be improved by receiving the allowable deviation range input by the treating physician.

For example, it is assumed that the identity information and the affected part information of a certain patient are a 6-year-old male and a leg tumor respectively. As the movement range and the number of times of movement of a male child are relatively lager generally and the tumor is located in the leg, for avoiding the problem that the positioning marker at the affected part deviates a relatively larger number of times because the patient may move frequently, the treating physician may set a relatively larger allowable deviation range, such as 0 to 5 mm, for this patient. It is assumed that the identity information and the affected part information of a certain patient are a 26-year-old female and a leg tumor respectively, a relatively smaller allowable deviation range, such as 0 to 3 mm, may be set for this patient. The treating physician may output the set allowable deviation range to the apparatus 01 for adjusting the position.

In step 304, whether the deviation between the real-time position and the reference position is greater than the allowable deviation range is detected.

In the embodiment of the present disclosure, when the deviation between the real-time position and the reference position is greater than the allowable deviation range, the deviation between the position of the positioning marker and the reference position is relatively larger. At this time, radiation rays emitted by the radiation source may irradiate the normal tissues of the patient, causing unpredictable injury to the patient. Therefore, the apparatus 01 for adjusting the position may calculate a distance (deviation) between the acquired real-time position and reference position, and compare this deviation with the allowable deviation range to detect whether the deviation between the real-time position and the reference position is greater than the allowable deviation range.

When the apparatus 01 for adjusting the position detects that the deviation between the real-time position and the reference position is greater than the allowable deviation range, step 305 below may be continued to be executed. When the apparatus 01 for adjusting the position detects that the deviation between the real-time position and the reference position is not greater than the allowable deviation range, step 306 below may be continued to be executed.

In step 305, the radiation source is turned off or alarm information is output, wherein the alarm information is configured to indicate to turn off the radiation source.

In the embodiment of the present disclosure, when the apparatus 01 for adjusting the position detects that the deviation between the real-time position and the reference position of the positioning marker is greater than the allowable deviation range, for preventing injury by the radiation source to the normal tissues of the patient, the apparatus 01 for adjusting the position may directly control the radiation source of the radiation therapy device to be turned off so as to stop radiation therapy. That is, the apparatus 01 for adjusting the position may actively control a working state of the radiation source. The reliability of radiation therapy can be effectively improved by directly turning off the radiation source.

Or the apparatus 01 for adjusting the position may also output the alarm information for indicating turn-off of the radiation source when detecting that the deviation between the real-time position and the reference position of the positioning marker is greater than the allowable deviation range.

Optionally, the apparatus 01 for adjusting the position may include an alarm apparatus or is connected to the alarm apparatus. When the deviation between the real-time position and the reference position is greater than the allowable deviation range, the apparatus 01 for adjusting the position may output the alarm information through the alarm apparatus. The treating physician may turn off the radiation source when receiving the alarm information.

For example, the alarm apparatus may be an acoustic-optical alarm and correspondingly the alarm information may be an acoustic-optical signal; or the alarm apparatus may also be a voice prompt component, and correspondingly the alarm information may be voice alarm information. For example, the voice alarm information may be a voice: "turn off the radiation source".

Figure 4:
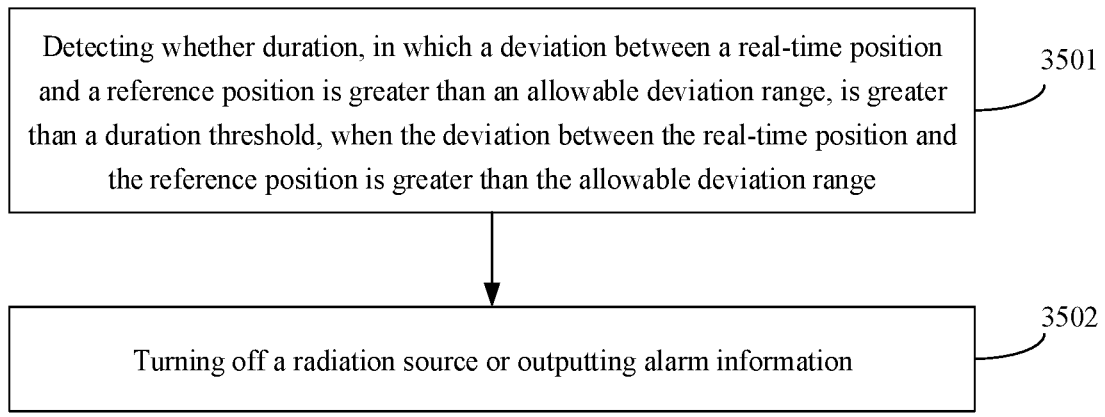
FIG. 4 is a flowchart of a method for turning off a radiation source and/or outputting alarm information when a deviation between a real-time position and a reference position is greater than an allowable deviation range according to an embodiment of the present disclosure.

FIG. 4 is a flowchart of a method for turning off a radiation source or outputting alarm information when a deviation between a real-time position and a reference position is greater than an allowable deviation range according to an embodiment of the present disclosure. As shown in FIG. 4, the method may include the following steps.

In step 3051, when the deviation between the real-time position and the reference position is greater than the allowable deviation range, whether duration in which the deviation between the real-time position and the reference position is greater than the allowable deviation range is greater than a duration threshold is detected.

In the embodiment of the present disclosure, for ensuring the efficiency of radiation therapy, there may be no need to turn off the radiation source when the duration in which the deviation between the real-time position and the reference position is greater than the allowable deviation range is relatively short. Therefore, the apparatus 01 for adjusting the position may also detect whether the duration in which the deviation between the real-time position and the reference position is greater than the allowable deviation range is greater than the duration threshold. The duration threshold may refer to a duration threshold preset in the apparatus 01 for adjusting the position, and for different identity information and different affected part information, the duration threshold may be different. That is, the apparatus 01 for adjusting the position may pre-store a corresponding relationship among the identity information and the affected part information of the patient and the duration threshold, so that the apparatus 01 for adjusting the position may determine the duration threshold corresponding to the patient based on the acquired identity information and affected part information of the patient with direct reference to the corresponding relationship. That is, the apparatus 01 for adjusting the position may acquire the duration threshold corresponding to a patient, who has a similar or the same identity information and the affected part information of the patient from the corresponding relationship, and determine the acquired duration threshold as the duration threshold of the patient.

When the apparatus for adjusting the position detects that the duration in which the deviation between the real-time position and the reference position is greater than the allowable deviation range is greater than the duration threshold, step 3052 below may be continued to be executed. When the apparatus for adjusting the position detects that the duration in which the deviation between the real-time position and the reference position is greater than the allowable deviation range is not greater than the duration threshold, step 306 below may be continued to be executed. That is, it is possible to prompt the patient to adjust his/her position for continuously performing radiation therapy on him/her.

For example, it is assumed that the deviation between the real-time position and the reference position detected by the apparatus 01 for adjusting the position is 5 mm and the acquired allowable deviation range is 3 mm, the apparatus 01 for adjusting the position may determine that the deviation between the real-time position and the reference position is greater than the allowable deviation range. At this time, the apparatus 01 for adjusting the position may continue to detect whether the duration in which the deviation between the real-time position and the reference position is greater than the allowable deviation range is greater than the duration threshold. It is assumed that the duration threshold is 2 s, and the duration in which the deviation between the real-time position and the reference position is greater than the allowable deviation range, detected by the apparatus 01 for adjusting the position, is 3 s, the apparatus 01 for adjusting the position may determine that the duration in which the deviation between the real-time position and the reference position is greater than the allowable deviation range is greater than the duration threshold. At this time, the apparatus 01 for adjusting the position may continue to perform step 3052 below.

In step 3052, the radiation source is turned off or the alarm information is output.

In the embodiment of the present disclosure, when the apparatus 01 for adjusting the position detects that the duration in which the deviation between the real-time position and the reference position is greater than the allowable deviation range is greater than the duration threshold, the apparatus 01 for adjusting the position may directly turn off the radiation source or output the alarm information for prompting the treating physician to turn off the radiation source.

In step 306, the position adjustment information is output, by means of the display and/or the voice, based on the real-time position, the reference position and the allowable deviation range.

In the embodiment of the present disclosure, when the apparatus for adjusting the position detects that the deviation between the real-time position and the reference position is not greater than the allowable deviation range or detects that the deviation between the real-time position and the reference position is greater than the allowable deviation range, but the duration in which the deviation between the real-time position and the reference position is greater than the allowable deviation range is not greater than the duration threshold, the apparatus for adjusting the position may output the position adjustment information, by means of the display and/or the voice, based on the real-time position, the reference position and the allowable deviation range.

In addition, in the embodiment of the present disclosure, after the patient adjusts his/her position based on the position adjustment information, the apparatus 01 for adjusting the position may continue to acquire the real-time position of the positioning marker after the patient adjusts his/her position, and output this acquired real-time position to the patient as the position adjustment information, so that the patient may continue to pertinently adjust his/her position based on his real-time adjustment situation.

As one optional embodiment, the position adjustment information may include: a designated coordinate system and relative positions of the real-time position and the reference position in the designated coordinate system. The apparatus for adjusting the position may output the position adjustment information by means of the display and/or the voice.

In this embodiment, the description is given with an example that the position adjustment information is output by means of the display.

In the embodiment of the present disclosure, the apparatus 01 for adjusting the position may include a display component or may be connected to the display component. The apparatus 01 for adjusting the position may output the position adjustment information through the display component.

The designated coordinate system may include a device coordinate system corresponding to the radiation therapy device or an infrared coordinate system of the position tracking system. In addition, the designated coordinate system displayed on the display component may be a six-dimensional coordinate system. That is, the display component may display a three-dimensional picture of a six-dimensional space.

Optionally, the position adjustment information may further include: a position of the allowable deviation range in the designated coordinate system, and/or a history motion track of the positioning marker.

Correspondingly, the apparatus 01 for adjusting the position may display the designated coordinate system, the relative positions of the real-time position and the reference position in the designated coordinate system and the allowable deviation range on the display component, so that the patient may adjust his/her position by observing the position adjustment information displayed on the display component.

Figure 5:
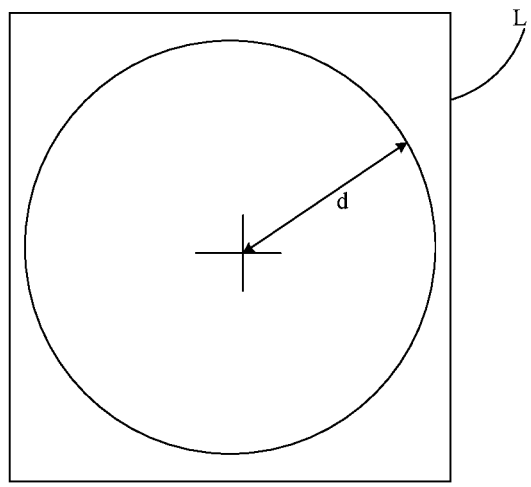
FIG. 5 is a diagram of a reference position of a positioning marker and an allowable deviation range which are displayed on a display component according to an embodiment of the present disclosure.

For example, FIG. 5 is a diagram of a reference position of a positioning marker and an allowable deviation range which are displayed on a display component L according to an embodiment of the present disclosure. As shown in FIG. 5, the apparatus 01 for adjusting the position may display the acquired reference position of the positioning marker on the display component L by using a cross mark. Or the apparatus 01 for adjusting the position may also display the acquired reference position of the positioning marker on the display component L by using a dot sign. The embodiment of the present disclosure does not limit a display form of the reference position of the positioning marker.

Further, as shown in FIG. 5, when displaying the allowable deviation range, the apparatus 01 for adjusting the position may determine a circle with the reference position as a center of the circle and the upper limit d of the distance value as a radius in the designated coordinate system, and display the circle. A range defined by the circle is the allowable deviation range of the affected part.

Figure 6:
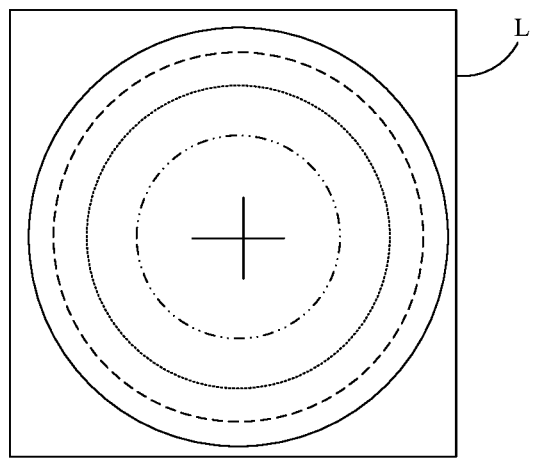
FIG. 6 is another diagram of a reference position of a positioning marker and an allowable deviation range which are displayed on a display component according to an embodiment of the present disclosure.

Optionally, the apparatus 01 for adjusting the position may divide the acquired allowable deviation range into different levels based on the size of the range, so that the patient may determine whether the position needs to be adjusted based on the different levels. FIG. 6 is a diagram of the allowable deviation range divided into four levels according to an embodiment of the present disclosure. In FIG. 6, a total of four circles are included, and the four circles may represent four different levels of the allowable deviation ranges respectively.

Figure 7:
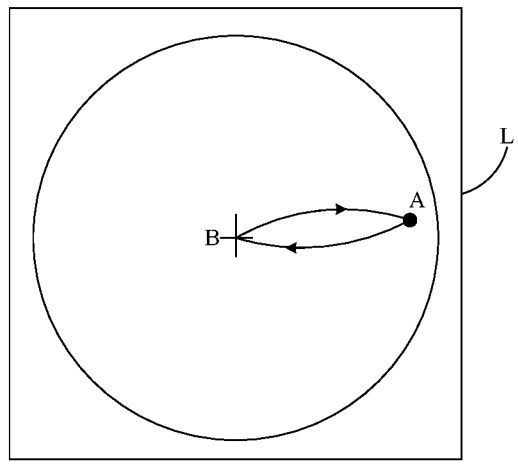
FIG. 7 is a diagram of a reference position and a real-time position of a positioning marker and an allowable deviation range which are displayed on a display component according to an embodiment of the present disclosure.

Further, FIG. 7 is a diagram of relative positions of a real-time position and a reference position in a designated coordinate system and an allowable deviation range which are displayed on a display component L according to an embodiment of the present disclosure. As shown in FIG. 7, the display component L may identify the reference position with a cross, such as a cross mark B in FIG. 7, identify the real-time position with a dot, such as a dot A in FIG. 7, and identify the allowable deviation range with a circle. At this time, the patient may observe that the positioning marker of the affected part is about to exceed the allowable deviation range, and that the reference position of the positioning marker of the affected part is located at the cross mark B, and then adjust his/her position, so that the positioning marker moves towards the cross mark.

Optionally, the history motion track of the positioning marker may also be displayed in real time on the display component L. The apparatus 01 for adjusting the position may also store the history motion track of the positioning marker, so that the treating physician may determine a movement range and the number of times of movement of the patient based on the history motion track of the positioning marker.

Optionally, the display component may be a display screen directly disposed above the treatment couch in the radiation therapy device. For facilitating observation by the patient, the display screen may be disposed in parallel with the treatment couch, and the display screen may be disposed within a line-of-sight range that is convenient for observation by the patient. Or the display component may also be glasses with a display screen. The patient may observe the position adjustment information by only wearing the glasses including the display screen, thereby improving the convenience of observation by the patient.

It should be noted that in the embodiment of the present disclosure, the real-time position, the reference position, the allowable deviation range and the motion track may also be displayed through the display component with different display effects (different colors). By means of the display with different display effects, it is convenient for the patient to observe, thereby improving the efficiency of adjusting the position by the patient.

Correspondingly, as shown in FIG. 6, when the apparatus 01 for adjusting the position divides the allowable deviation range into a plurality of levels, the display component L may also display the different levels of the allowable deviation range with different display effects (different lines), so that the patient determines which level of the allowable deviation range the positioning marker is currently located, and then determines whether the position needs to be adjusted.

As another optional embodiment, the apparatus 01 for adjusting the position may also determine a position adjustment mode based on the deviation between the real-time position and the reference position and the deviation is acquired in advance; and then output the position adjustment information including the position adjustment mode by means of the display and/or the voice.

In this embodiment, the description is given with an example that the position adjustment information including the position adjustment mode is output by means of the voice.

In the embodiment of the present disclosure, the apparatus 01 for adjusting the position may include a voice prompt component. For example, the apparatus 01 for adjusting the position may include a speaker, and may directly broadcast the determined position adjustment mode to the patient through the speaker. Or the apparatus 01 for adjusting the position may be connected to the voice prompt component. For example, the voice prompt component may include a speaker box or an earphone. The apparatus 01 for adjusting the position may establish a connection with the voice prompt component in a wired or wireless manner. Correspondingly, the apparatus 01 for adjusting the position may send the determined position adjustment mode to the voice prompt component, and then the voice prompt component may broadcast the position adjustment information including the position adjustment mode to the patient.

The position adjustment mode may include a position adjustment direction and a position adjustment distance. The apparatus 01 for adjusting the position may calculate the position adjustment direction and the distance needing to be adjusted through a preset algorithm based on the deviation between the real-time position and the reference position. The preset algorithm refers to such an algorithm that determines the adjustment direction and the adjustment distance based on the deviation between the real-time position and the reference position and relative directions of the real-time position and the reference position so as to align the real-time position with the reference position. Further, the apparatus 01 for adjusting the position may send the determined position adjustment mode to the voice prompt component, and the voice prompt component may notify the patient of the position adjustment mode through voice broadcast.

For example, it is assumed that the position adjustment mode determined by the apparatus 01 for adjusting the position based on the deviation between the real-time position and the reference position is: move X mm to the right, and the voice prompt component is an earphone connected to the apparatus 01 for adjusting the position. The apparatus 01 for adjusting the position may broadcast the position adjustment information, i.e., move X mm to the right, to the patient through the earphone, so that the patient may adjust his/her position based on the position adjustment information.

It should be noted that the method for adjusting the position including steps 301-306 described above is also applicable to the process of positioning the patient. When positioning the patient, the treating physician may determine whether the positioning marker of the affected part is within the allowable deviation range based on the position adjustment information, and determine the deviation between the real-time position and the reference position of the positioning marker of the affected part. In addition, the treating physician may train the patient to actively participate in positioning based on the position adjustment information, thereby ensuring the accuracy of the positioning.

In the embodiment of the present disclosure, the apparatus 01 for adjusting the position may also store the acquired reference position and the acquired allowable deviation range of the positioning marker of each patient, and the acquired motion track of the patient, after radiation therapy is performed on each patient. For example, the apparatus 01 for adjusting the position may store the reference positions and the allowable deviation ranges of the positioning markers of various patients, and the motion tracks of the patients in a classified manner. In addition, the apparatus 01 for adjusting the position may store the acquired reference positions and the acquired allowable deviation ranges of the positioning markers of various patients, and the acquired motion tracks of the patients in a classified manner based on features such as the identity information of the patients or the affected part information of the patients. In this way, when treating a certain patient, the treating physician may make a preliminary treatment plan for the patient based on reference positions of the positioning markers, allowable deviation ranges and motion tracks of the patient, which correspond to different types of patients and are stored in the apparatus 01 for adjusting the position. Therefore, the efficiency of performing radiation therapy on the patient is improved.

It should also be noted that due to relatively poorer self-control ability, some patients may not be able to adjust and control their positions by themselves. Therefore, before performing radiation therapy on the patient, the treating physician may also perform a simulated radiation therapy on the patient firstly so as to determine whether the method for adjusting the position including steps 301 to 306 above is suitable for the patient. That is, when performing simulated treatment on a certain patient, the treating physician may determine the movement range and the number of times of movement of the patient based on the output position adjustment information. When the movement range and the number of times of movement of the patient are relatively larger and it is difficult for the patient to adjust and control his/her position, the treating physician may directly anaesthetize the patient with a drug before performing radiation therapy on this patient to further ensure the reliability of radiation therapy. The simulated radiation therapy refers to a method for performing a simulated radiation therapy on patients without turning on the radiation source.

In step 307, the number of times of deviation that the deviation between the real-time position and the reference position is greater than the allowable deviation range within a preset time period is acquired.

In the embodiment of the present disclosure, for determining the movement range and the number of times of movement of the patient, that is, for determining whether the patient moves, before radiation therapy is performed on the patient, the apparatus 01 for adjusting the position may also acquire the number of times of a deviation which is between the real-time position and the reference position and is greater than the allowable deviation range within the preset time period. The preset time period refers to a time period preset in the apparatus 01 for adjusting the position and may be 10 minutes or 1 hour.

In step 308, a positioning mode for the patient is determined based on the number of times of the deviation.

In the embodiment of the present disclosure, the positioning mode may include a traumatic positioning and a non-traumatic positioning. The traumatic positioning refers to a positioning mode in which the patient is fixed on the treatment couch with tools such as head nails and head racks. The non-traumatic positioning refers to a positioning mode in which the patient is fixed on the treatment couch with a facial mask. For patients with the number of times of movement and the movement range being relatively larger, they may be fixed on the treatment couch in the traumatic positioning mode before the radiation therapy to ensure the reliability and precision of radiation therapy. Correspondingly, for patients with the number of times of movement and the movement range being relatively smaller, they may be fixed on the treatment couch in the non-traumatic positioning mode before the radiation therapy.

In the embodiment of the present disclosure, when the apparatus 01 for adjusting the position detects that the number of times of deviation is greater than a threshold of the number of times, it may be determined that the number of times of movement and the movement range of the patient are relatively larger, that is, it may be determined that the positioning mode for this type of patient may be traumatic positioning. When the apparatus 01 for adjusting the position detects that the number of times of deviation is not greater than the threshold of the number of times, it may be determined that the number of times of movement and the movement range of the patient are relatively smaller, that is, it may be determined that the positioning mode for this type of patient may be non-traumatic positioning. The threshold of the number of times may refer to a threshold of the number of times preset in the apparatus 01 for adjusting the position. The thresholds of the number of times may be different for different patients.

For example, it is assumed that the threshold of the number of times is 6, the preset time period is 1 hour, and the number of times of a deviation is 5. The deviation is between the real-time position and the reference position, and is greater than the allowable deviation range and acquired by the apparatus 01 for adjusting the position within 1 hour. The apparatus 01 for adjusting the position may detect that the number of times of deviation is less than the threshold of the number of times, and the apparatus 01 for adjusting the position may determine that the positioning mode for this patient is non-traumatic positioning in this case.

Optionally, in the embodiment of the present disclosure, the apparatus 01 for adjusting the position may also acquire other information of the patient (such as identity information and affected part information of the patient). The apparatus 01 for adjusting the position may score the number of times of movement and the movement range of the patient with reference to the identity information and the affected part information of the patient and the number of times of deviation before radiation therapy is performed on the patient. Correspondingly, when the calculated score is greater than a score threshold, it may be determined that the positioning mode for the patient is the traumatic positioning; and when the calculated score is not greater than the score threshold, it may be determined that the positioning mode for the patient is the non-traumatic positioning. The score threshold may refer to a score value pre-stored in the apparatus 01 for adjusting the position. By determining the positioning mode of the patient with reference to various kinds of information, the determined positioning mode may be more targeted.

It should be noted that the order of steps of the method for adjusting the position according to the embodiment of the present disclosure may be adjusted properly and the steps may also be correspondingly increased or decreased according to the situation. Changed methods that would be readily conceived by any person skilled in the art within the scope of the technology disclosed in the present disclosure should be within the scope of protection of the present disclosure and thus will not be described herein.

In summary, in the method for adjusting the position according to the embodiment of the present disclosure, the position adjustment information for prompting the patient to adjust his/her position may be output, by means of the display and/or the voice, based on the acquired real-time position of the positioning marker preset at the affected part and the acquired reference position of the positioning marker. As the method may allow the patient to adjust his/her position by himself/herself based on the output position adjustment information, there is no need for frequently moving the treatment couch. Therefore, the problem that the precision of radiation therapy is affected due to an accumulated mechanical error caused by constantly moving the treatment couch is avoided.

Figure 8:
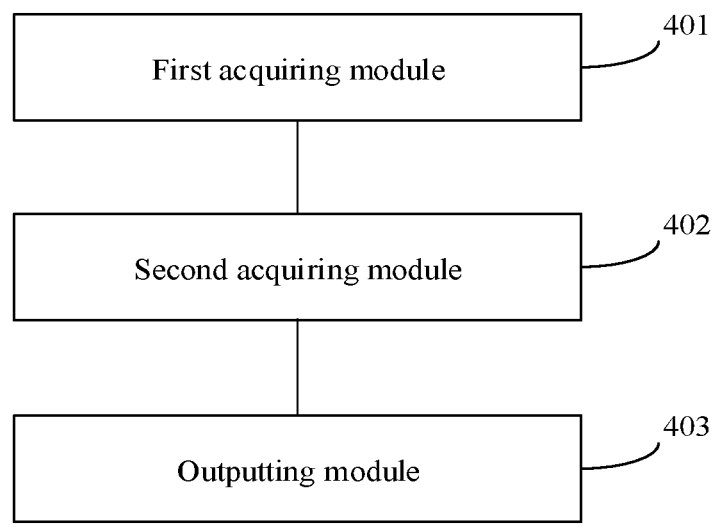
FIG. 8 is a block diagram of an apparatus for adjusting a position according to an embodiment of the present disclosure.

FIG. 8 is a block diagram of an apparatus for adjusting a position according to an embodiment of the present disclosure. As shown in FIG. 8, the apparatus for adjusting the position may include:
- a first acquiring module 401 configured to acquire a real-time position of a positioning marker preset at an affected part;
- a second acquiring module 402 configured to acquire a reference position of the positioning marker; and
- an outputting module 403 configured to output position adjustment information based on the real-time position and the reference position by means of a display and/or a voice, wherein the position adjustment information is configured to prompt a patient to adjust his/her position.

In summary, for the apparatus for adjusting the position according to the embodiment of the present disclosure, the apparatus includes the outputting module configured to output the position adjustment information for prompting the patient to adjust his/her position, by means of the display and/or the voice, based on the real-time position of the positioning marker preset at the affected part acquired by the first acquiring module and the reference position of the positioning marker acquired by the second acquiring module. As the apparatus may allow the patient to adjust his/her position by himself/herself based on the output position adjustment information, there is no need for frequently moving a treatment couch. Therefore, the problem that the precision of radiation therapy is affected due to an accumulated mechanical error caused by constantly moving the treatment couch is avoided.

Optionally, in the embodiment of the present disclosure, the position adjustment information may include: a designated coordinate system and relative positions of the real-time position and the reference position in the designated coordinate system.

Figure 9:
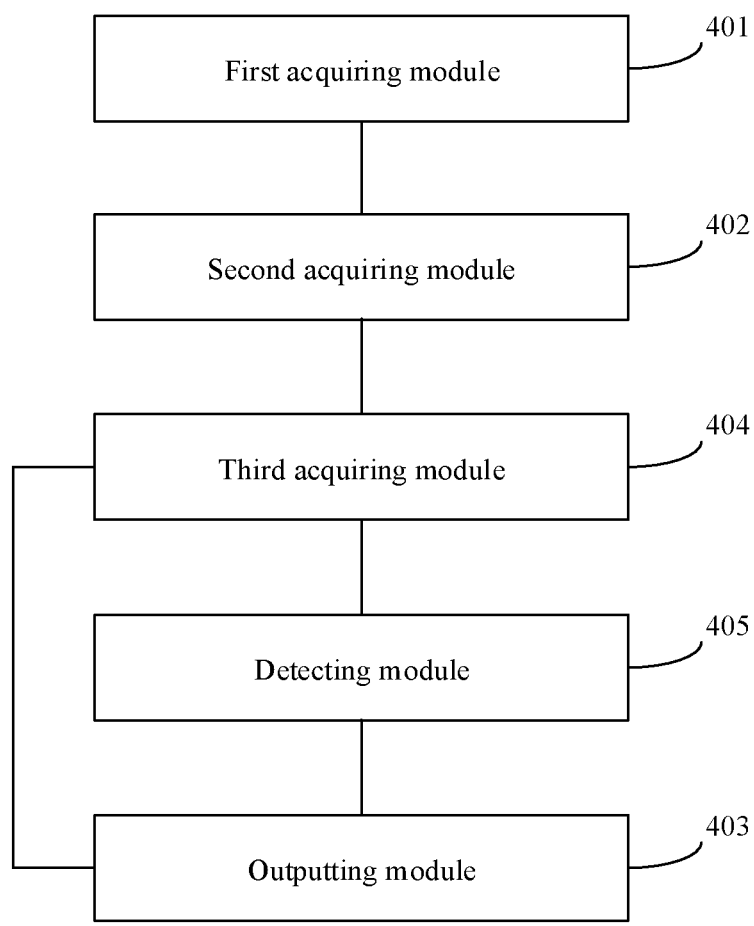
FIG. 9 is a block diagram of another apparatus for adjusting a position according to an embodiment of the present disclosure.

FIG. 9 is a block diagram of another apparatus for adjusting a position according to an embodiment of the present disclosure. As shown in FIG. 9, the apparatus for adjusting the position may further include:
- a third acquiring module 404 configured to acquire an allowable deviation range.

Correspondingly, the outputting module 403 may be configured to output the position adjustment information, by means of the display and/or the voice, based on the real-time position, the reference position and the allowable deviation range.

Optionally, the third acquiring module 404 may be configured to acquire identity information and affected part information of the patient, and acquire an allowable deviation range corresponding to the identity information and the affected part information.

Further, referring to FIG. 9, the apparatus for adjusting the position may further include:
- a detecting module 405 configured to detect whether a deviation between the real-time position and the reference position is greater than the allowable deviation range after the reference position of the positioning marker is acquired.

Optionally, the outputting module 403 may further be configured to turn off a radiation source or output alarm information when the deviation between the real-time position and the reference position is greater than the allowable deviation range. The alarm information may be configured to indicate to turn off the radiation source.

Optionally, the outputting module 403 may further be configured to:
detect whether a duration in which the deviation between the real-time position and the reference position is greater than the allowable deviation range is greater than a duration threshold when the deviation between the real-time position and the reference position is greater than the allowable deviation range; and turn off the radiation source or output the alarm information when the duration in which the deviation between the real-time position and the reference position is greater than the allowable deviation range is greater than the duration threshold.

Optionally, in the embodiment of the present disclosure, the position adjustment information may further include: a position of the allowable deviation range in the designated coordinate system, and/or a history motion track of the positioning marker.

Figure 10:
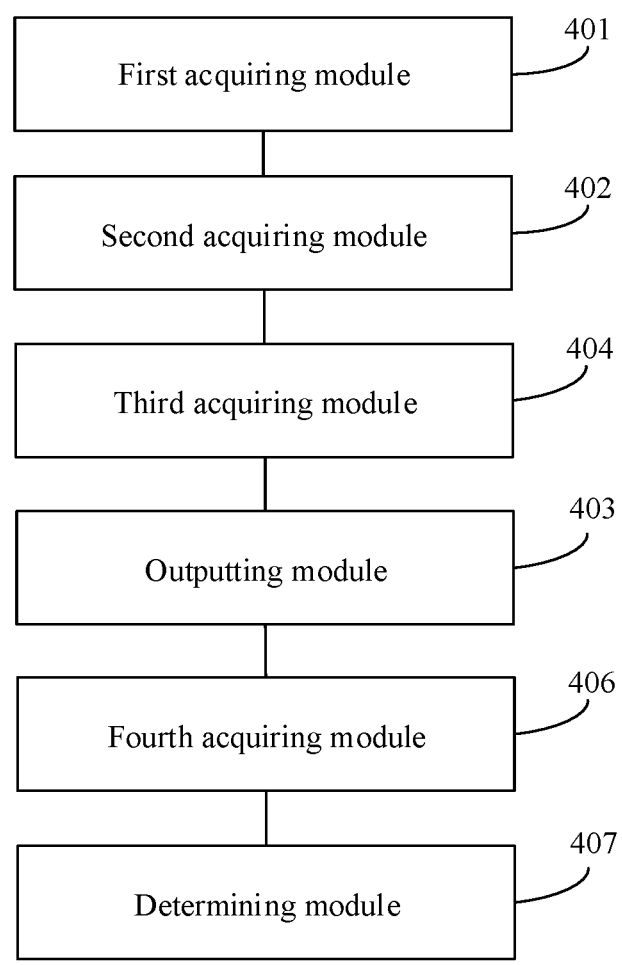
FIG. 10 is a block diagram of still another apparatus for adjusting a position according to an embodiment of the present disclosure.

FIG. 10 is a block diagram of still another apparatus for adjusting a position according to an embodiment of the present disclosure. As shown in FIG. 10, the apparatus for adjusting the position may further include:
- a fourth acquiring module 406 configured to acquire the number of times of a deviation which is between the real-time position and the reference position and is greater than the allowable deviation range within a preset time period; and
- a determining module 407 configured to determine a positioning mode for the patient based on the number of times of deviation.

The positioning mode may include a traumatic positioning and a non-traumatic positioning.

Optionally, the determining module 407 may be configured to:

determine that the positioning mode for the patient is the traumatic positioning when the number of times of deviation is greater than a threshold of the number of times; and determine that the positioning mode for the patient is non-the traumatic positioning when the number of times of deviation is not greater than a threshold of the number of times.

Optionally, the outputting module 403 may be configured to display the real-time position and the reference position with different display effects.

Optionally, the outputting module 403 may be configured to:

determine a position adjustment mode based on a deviation between the real-time position and the reference position; and output the position adjustment information including the position adjustment mode by means of the display and/or the voice.

Optionally, the second acquiring module 402 may be configured to:

acquire a position of the positioning marker after the patient has been positioned, and determine the acquired position as the reference position; or acquire the reference position from a treatment plan before the radiation therapy.

In summary, for the apparatus for adjusting the position according to the embodiment of the present disclosure, the apparatus includes the outputting module configured to output the position adjustment information for prompting the patient to adjust his/her position, by means of the display and/or the voice, based on the real-time position of the positioning marker preset at the affected part acquired by the first acquiring module and the reference position of the positioning marker acquired by the second acquiring module. As the apparatus may allow the patient to adjust his/her position by himself/herself based on the output position adjustment information, there is no need for frequently moving a treatment couch. Therefore, the problem that the precision of radiation therapy is affected due to an accumulated mechanical error caused by constantly moving the treatment couch is avoided.

With regard to the apparatus for adjusting the position in the above embodiments, the specific mode in which the respective modules perform the operations has been described in detail in embodiments of the related method, and will not be explained in detail herein.

An embodiment of the present disclosure provides an apparatus for adjusting a position. The apparatus for adjusting the position includes: a processor and a memory. The memory stores an instruction therein which may be loaded and executed by the processor to implement the method for adjusting the position as shown in any of FIGS. 2-4.

In addition, an embodiment of the present disclosure provides a storage medium. The storage medium stores an instruction therein. The storage medium, when running on a processing component, enables the processing component to perform the method for adjusting the position as shown in any of FIGS. 2-4

An embodiment of the present disclosure further provides a radiation therapy system. The radiation therapy system may include the apparatus for adjusting the position as shown in any of FIGS. 8-10 and a position tracking system. FIG. 1 shows a structural diagram of the radiation therapy system.

It should be understood that the term "a plurality of" mentioned herein means two or more. The term "and/or" describes an association relationship of associated objects, indicating that there may be three types of relationships. For example, A and/or B may indicate three situations: A exists alone, A and B exist simultaneously, and B exists alone. The character "/" generally indicates that the associated objects are in an "or" relationship.

A person skilled in the art may clearly understand that for the sake of convenience and conciseness in description, the specific work processes of the above apparatuses and modules may make reference to corresponding processes in the above method embodiments and are not further described herein.

The above descriptions are only preferred embodiments of the present disclosure, and are not intended to limit the present disclosure. Any modifications, equivalent replacements, improvements and the like made within the spirit and principles of the present disclosure should be included within the scope of protection of the present disclosure.

What is claimed is:

1. A method for adjusting a position, comprising:
   acquiring a real-time position of a positioning marker preset at an affected part;
   acquiring a reference position of the positioning marker;
   acquiring an allowable deviation range;
   outputting position adjustment information, by means of a display and/or a voice, based on the real-time position and the reference position and the allowable deviation range, wherein the position adjustment information is configured to prompt a patient to adjust his/her position;
   acquiring a number of times of a deviation which is between the real-time position and the reference position and is greater than the allowable deviation range, within a preset time period; and
   determining a positioning mode for the patient based on the number of times of the deviation, wherein the positioning mode comprises a traumatic positioning or a non-traumatic positioning.

2. The method according to claim 1, wherein
   the position adjustment information comprises: a designated coordinate system and relative positions of the real-time position and the reference position in the designated coordinate system.

3. The method according to claim 2, wherein
   the position adjustment information further comprises: a position of the allowable deviation range in the designated coordinate system, and/or a history motion track of the positioning marker.

4. The method according to claim 1, wherein after acquiring the reference position of the positioning marker, the method further comprises:
   detecting whether a deviation between the real-time position and the reference position is greater than the allowable deviation range; and
   turning off a radiation source or outputting alarm information in response to the deviation between the real-time position and the reference position being greater than the allowable deviation range, wherein the alarm information is configured to indicate to turn off the radiation source.

5. The method according to claim 4, wherein turning off the radiation source or outputting the alarm information in response to the deviation between the real-time position and the reference position being greater than the allowable deviation range comprises:
   detecting whether duration, in which the deviation between the real-time position and the reference position is greater than the allowable deviation range, is greater than a duration threshold in response to the deviation between the real-time position and the reference position being greater than the allowable deviation range; and turning off the radiation source or outputting the alarm information in response to the duration, in which the deviation between the real-time position and the reference position is greater than the allowable deviation range, being greater than the duration threshold.

6. The method according to claim 1, wherein determining the positioning mode for the patient based on the number of times of the deviation comprises:

determining that the positioning mode for the patient is the traumatic positioning in response to the number of times of the deviation being greater than a threshold of the number of times; or determining that the positioning mode for the patient is the non-traumatic positioning in response to the number of times of the deviation being not greater than the threshold of the number of times.

7. The method according to claim 1, wherein outputting the position adjustment information by means of the display comprises:

displaying the real-time position and the reference position with different display effects.

8. The method according to claim 1, wherein outputting the position adjustment information by means of the display and/or the voice comprises:

determining a position adjustment mode based on a deviation between the real-time position and the reference position; and outputting the position adjustment information comprising the position adjustment mode by means of the display and/or the voice.

9. The method according to claim 1, wherein acquiring the reference position of the positioning marker comprises:

acquiring a position of the positioning marker after the patient has been positioned, and determining the acquired position as the reference position; or acquiring the reference position from a treatment plan before a radiation therapy.

10. A non-transitory storage medium storing an instruction therein, wherein the storage medium, when running on a processing component, enables the processing component to perform the method for adjusting the position as defined in claim 1.

11. An apparatus for adjusting a position, comprising a processor and a memory, wherein the memory stores an instruction therein which is loaded and executed by the processor, and the processor is configured to:

acquire a real-time position of a positioning marker preset at an affected part;

acquire a reference position of the positioning marker;

acquire an allowable deviation range;

output position adjustment information, by means of a display and/or a voice, based on the real-time position and the reference position and the allowable deviation range, wherein the position adjustment information is configured to prompt a patient to adjust his/her position;

acquire a number of times of a deviation which is between the real-time position and the reference position and is greater than the allowable deviation range, within a preset time period; and determine a positioning mode for the patient based on the number of times of the deviation, wherein the positioning mode comprises a traumatic positioning or a non-traumatic positioning.

12. A radiation therapy system, comprising the apparatus for adjusting the position as defined in claim 11, and a position tracking system.

13. The apparatus according to claim 11, wherein the processor is further configured to:

detect whether a deviation between the real-time position and the reference position is greater than the allowable deviation range after the reference position of the positioning marker is acquired; and turn off a radiation source or output alarm information when the deviation between the real-time position and the reference position is greater than the allowable deviation range, wherein the alarm information is configured to indicate to turn off the radiation source.

14. The apparatus according to claim 13, wherein the processor is further configured to:

detect whether duration, in which the deviation between the real-time position and the reference position is greater than the allowable deviation range, is greater than a duration threshold, when the deviation between the real-time position and the reference position is greater than the allowable deviation range; and turn off the radiation source or output the alarm information when the duration, in which the deviation between the real-time position and the reference position is greater than the allowable deviation range, is greater than the duration threshold.

15. The apparatus according to claim 11, wherein the processor is further configured to display the real-time position and the reference position with different display effects.

16. The apparatus according to claim 11, wherein the processor is further configured to:

determine a position adjustment mode based on a deviation between the real-time position and the reference position; and output the position adjustment information comprising the position adjustment mode by means of the display and/or the voice.

* * * * *